(12) United States Patent
Jang et al.

(10) Patent No.: US 11,083,979 B2
(45) Date of Patent: Aug. 10, 2021

(54) SOLVENT SEPARATION METHOD AND SOLVENT SEPARATION APPARATUS

(71) Applicant: LG CHEM, LTD., Seoul (KR)

(72) Inventors: Sung Keun Jang, Daejeon (KR); Dae Young Shin, Daejeon (KR); Chang Hoe Heo, Daejeon (KR); Seung Won Choi, Daejeon (KR); Eun Jung Joo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/495,535

(22) PCT Filed: Aug. 30, 2018

(86) PCT No.: PCT/KR2018/010096
§ 371 (c)(1),
(2) Date: Sep. 19, 2019

(87) PCT Pub. No.: WO2019/054671
PCT Pub. Date: Mar. 21, 2019

(65) Prior Publication Data
US 2020/0094164 A1    Mar. 26, 2020

Related U.S. Application Data

(63) Continuation of application No. PCT/KR2018/010096, filed on Aug. 30, 2018.

(30) Foreign Application Priority Data

Sep. 12, 2017  (KR) .......... 10-2017-0116740
Aug. 27, 2018  (KR) .......... 10-2018-0100355

(51) Int. Cl.
*B01D 3/06*      (2006.01)
*B01D 11/04*     (2006.01)
(Continued)

(52) U.S. Cl.
CPC .......... *B01D 11/0403* (2013.01); *B01D 3/065* (2013.01); *B01J 3/008* (2013.01);
(Continued)

(58) Field of Classification Search
CPC ............ B01D 11/0403; B01D 11/0292; B01D 11/0203; B01D 3/06; B01D 3/065;
(Continued)

(56) References Cited

U.S. PATENT DOCUMENTS 2,631,966 A * 3/1953 Francis .................. C10G 21/08
                                                              208/321
3,494,836 A * 2/1970 Standiford, Jr. .......... C02F 1/06
                                                              203/7
(Continued)

FOREIGN PATENT DOCUMENTS

CN  101502610 A   8/2009
CN  102085239 A   6/2011
(Continued)

OTHER PUBLICATIONS

Semenova et al., "Separation of supercritical CO2 and ethanol mixtures with an asymmetric polyimide membrane", Journal of Membrane Science, vol. 74, No. 1-2, pp. 131-139 (1992).
(Continued)

*Primary Examiner* — Joseph W Drodge
(74) *Attorney, Agent, or Firm* — Dentons US LLP

(57) ABSTRACT

A separation method and a separation apparatus for a solvent extracted by supercritical extraction. The separation method increases a solvent recovery rate by minimizing the amount of a solvent to be evaporated and lost since the pressure of a solvent is reduced by arranging two or more separators in series. The method includes: introducing a fluid having passed through a supercritical extractor into a first flash vessel; introducing the fluid which has passed through the
(Continued)

first flash vessel into a second flash vessel; and discharging and recovering the carbon dioxide and the solvent which have passed through the second flash vessel, respectively. The pressure of the first flash vessel is 40-100 bar, and the pressure of the second flash vessel is 1-30 bar. The fluid includes carbon dioxide and a solvent.

7 Claims, 2 Drawing Sheets

(51) Int. Cl.
*C07C 29/80* (2006.01)
*B01J 3/00* (2006.01)
(52) U.S. Cl.
CPC ....... *C07C 29/80* (2013.01); *B01J 2219/0004* (2013.01); *B01J 2219/00162* (2013.01)
(58) Field of Classification Search
CPC . B01D 11/04; B01D 11/0407; B01D 11/0488; B01D 11/0492; B01D 2011/007; B01J 3/008; B01J 2219/0004; B01J 2219/00162; C07C 29/80; C07C 29/86
USPC ......... 210/511, 634, 639; 422/256; 568/840, 568/868
See application file for complete search history.

(56) References Cited

U.S. PATENT DOCUMENTS

| | | | | |
|---|---|---|---|---|
| 4,252,548 A * | 2/1981 | Markbreiter | ......... | B01D 53/265 62/632 |
| 4,341,619 A * | 7/1982 | Poska | ................ | B01D 11/0203 208/390 |
| 4,349,415 A * | 9/1982 | DeFilippi | ............... | B01D 3/343 203/14 |
| 4,375,387 A * | 3/1983 | deFilippi | ................ | B01D 3/143 196/134 |
| 4,478,705 A * | 10/1984 | Ganguli | ............. | B01D 11/0407 208/102 |
| 4,877,530 A * | 10/1989 | Moses | ................ | B01D 11/0407 210/511 |
| 5,158,652 A | 10/1992 | Pucci et al. | | |
| 6,204,401 B1 | 3/2001 | Perrut et al. | | |
| 7,465,395 B2 * | 12/2008 | Carbonell | .......... | B01D 11/0288 134/13 |
| 2001/0050096 A1 * | 12/2001 | Costantini | ......... | H01L 21/67034 134/58 R |
| 2009/0026136 A1 * | 1/2009 | Beltz | ........................ | B08B 3/04 210/634 |
| 2009/0178693 A1 * | 7/2009 | Turner | .................. | B01D 53/00 134/10 |
| 2010/0267976 A1 * | 10/2010 | Chordia | ............. | B01D 11/0203 554/11 |
| 2011/0112329 A1 | 5/2011 | Waibel et al. | | |
| 2011/0201842 A1 | 8/2011 | Schon | | |
| 2015/0283477 A1 * | 10/2015 | Chess | ................ | B01D 11/0203 554/8 |
| 2018/0333757 A1 * | 11/2018 | Scalley | ................ | B01D 11/028 |

FOREIGN PATENT DOCUMENTS

| | | |
|---|---|---|
| CN | 102643714 A | 8/2012 |
| CN | 205145937 U | 4/2016 |
| JP | 61-238736 A | 10/1986 |
| JP | 62-29988 A | 2/1987 |
| JP | 62-29990 A | 2/1987 |
| JP | 63-174997 A | 7/1988 |
| JP | 05-305203 A | 11/1993 |
| JP | 06-007605 A | 1/1994 |
| JP | 06-063308 A | 3/1994 |
| KR | 10-0199224 B1 | 6/1999 |
| KR | 10-2000-0070518 A | 11/2000 |
| KR | 10-2002-0062287 A | 7/2002 |
| KR | 10-0675356 B1 | 2/2007 |
| WO | 2010/044990 A1 | 4/2010 |
| WO | 2017/137912 A1 | 8/2017 |

OTHER PUBLICATIONS

Ruiz-Rodriguez, et al., "Supercritical CO2 extraction applied toward the production of a functional beverage from wine", The Journal of Supercritical Fluids, vol. 61, Sep. 6, 2011, pp. 92-100, XP028342018, ISSN: 0896-8446.
Medina, et al., "Dealcoholisation of Cider by Supercritical Extraction with Carbon Dioxide", Journal of Chemical Technology and Biotechnology, vol. 68, No. 1, Jan. 1, 1997, pp. 14-18, XP000686496, ISSN: 0268-2575.
Teye, "Continuous flash extraction of alcohols from fermentation broth", Thesis submitted to the Faculty of the Virginia Polytechnic Institute and State University in partial fulfillment of the requirements of the degree of Master of Science in Biological Systems Engineering, Feb. 4, 2009, XP055679277, pp. 44, 59, 63.

* cited by examiner

SOLVENT SEPARATION METHOD AND SOLVENT SEPARATION APPARATUS

CROSS-REFERENCE TO RELATED APPLICATIONS

This application is the U.S. national stage of international application No. PCT/KR2018/010096 filed on Aug. 30, 2018, and claims the benefit of Korean Patent Application No. 10-2017-0116740, filed on Sep. 12, 2017, and Korean Patent Application No. 10-2018-0100355, filed on Aug. 27, 2018, in the Korean Intellectual Property Office, the disclosures of which are incorporated herein in their entirety by reference.

TECHNICAL FIELD

The present invention relates to a solvent separation method and a solvent separation apparatus for extracted solvent through supercritical extraction.

BACKGROUND ART

Supercritical fluids refer to fluids at temperatures or pressures above their critical points. The supercritical fluids have intermediate unique properties between gas and liquid such as viscosity and diffusion coefficient similar to gas, and density close to liquid, thereby being applied to various fields such as supercritical extraction, drying, polymerization, and dyeing. Representative liquid mixtures which may be separated by supercritical extraction are water and ethanol. Since the solubility of $CO_2$ is higher in ethanol than in water, only ethanol may be selectively extracted. Such supercritical extraction may replace conventional techniques such as distillation, liquid extraction and membrane separation, which were conventionally used for ethanol separation.

Meanwhile, after the extraction of ethanol, the extracted phase leaving the upper portion of the extracting tower becomes a ternary mixture containing $CO_2$, ethanol and a small amount of water. This fluid flows through a pressure reducing valve and flows into a flash vessel, where the pressure of the fluid is rapidly reduced and the fluid is separated into $CO_2$ and liquid ethanol, respectively. The $CO_2$ recovered in a gas phase is subjected to a heat exchange/pressurization process and then used for supercritical extraction, and the ethanol present in a liquid phase in the flash vessel is recovered in atmospheric pressure and room temperature conditions by opening a lower valve of the flash vessel. In this case, the liquid ethanol present in the flash vessel under the high pressure condition is discharged at atmospheric pressure, and some ethanol is vaporized to cause loss.

Accordingly, the inventors of the present invention have studied in order to recover ethanol as much as possible by minimizing the amount of the vaporized and lost ethanol in the step of recovering ethanol in the flash vessel, and as a result, have completed the present invention.

PRIOR ART DOCUMENT (Patent Document 1) Korean Patent Laid-Open Publication No. 2000-0070518 (published on Nov. 25, 2000)

DISCLOSURE OF THE INVENTION

Technical Problem

An aspect of the present invention is to reduce the pressure of the solvent extracted through the supercritical extraction stepwise and separate the solvent, thereby minimizing the amount of the solvent lost by vaporization and increasing the recovery rate of the solvent.

Technical Solution

According to an aspect of the present invention, there is provided a solvent separation method including:
1) introducing, into a first flash vessel, a fluid which includes carbon dioxide and a solvent and has passed through a supercritical extractor;
2) introducing, into a second flash vessel, the fluid which has passed through the first flash vessel; and
3) discharging and recovering the carbon dioxide and the solvent which have passed through the second flash vessel, respectively,
wherein the pressure of the first flash vessel is 40-100 bar, and the pressure of the second flash vessel is 1-30 bar.

According to another aspect of the present invention, there is provided a solvent separation apparatus including:
a) a first flash vessel into which a fluid, which includes carbon dioxide and a solvent and has passed a supercritical extractor, is introduced;
b) a second flash vessel into which the fluid having passed the first flash vessel, is introduced; and
c) a solvent recovery tank connected to a lower portion of the second flash vessel and configured to store the discharged and recovered solvent,
wherein the pressure of the first flash vessel is 40-100 bar, and the pressure of the second flash vessel is 1-30 bar.

Advantageous Effects

In a solvent separation method and a solvent separation apparatus according to embodiments of the present invention, two or more of flash vessels are arranged in series to decrease the pressure of a solvent stepwise, so that the amount of the solvent lost by vaporization is minimized to obtain an effect of increasing the solvent recovery rate.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Figure 1:
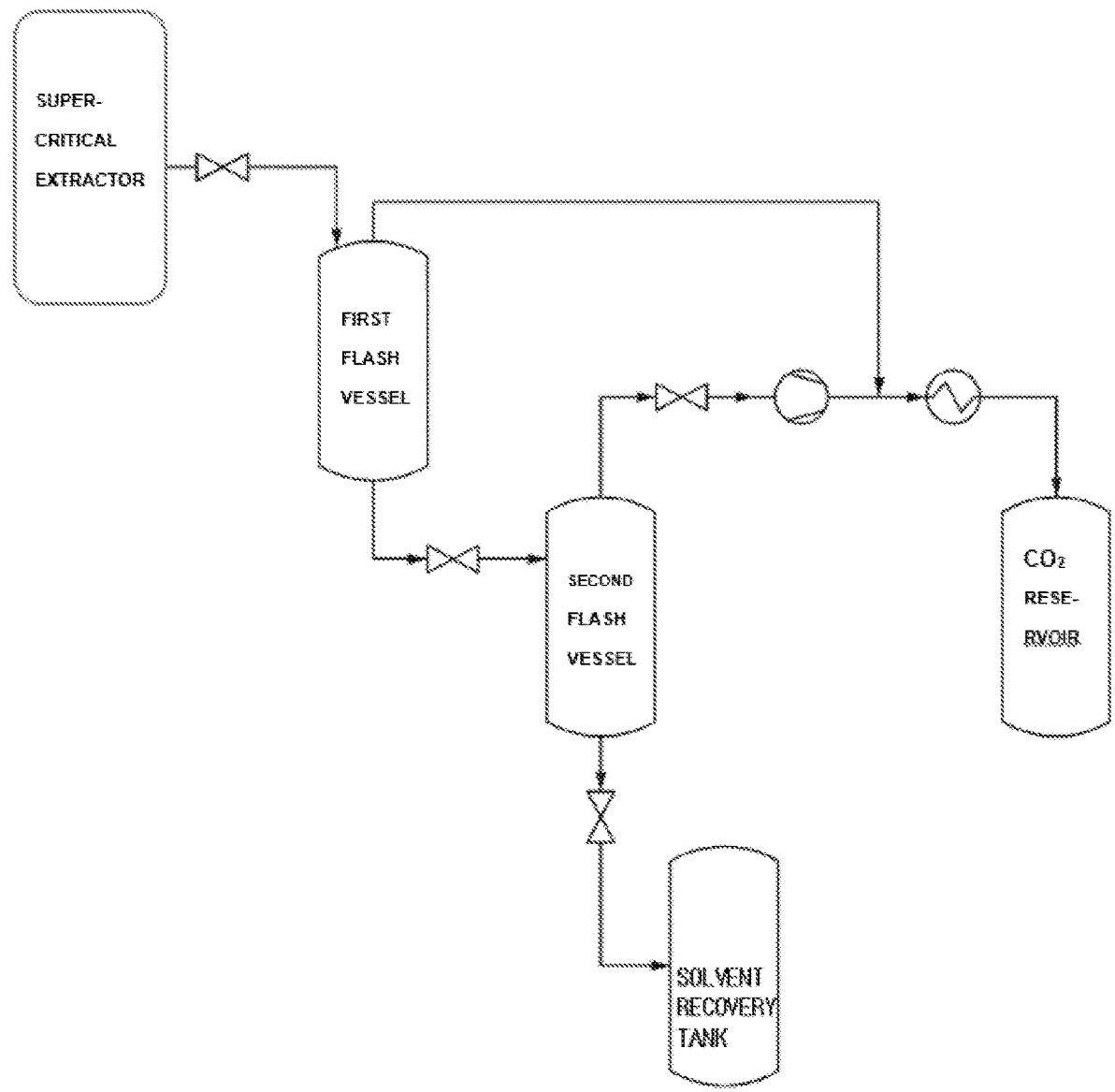
FIG. 1 is a schematic diagram schematically showing a solvent separation method and a solvent separation apparatus according to an embodiment of the present invention.
Figure 2:
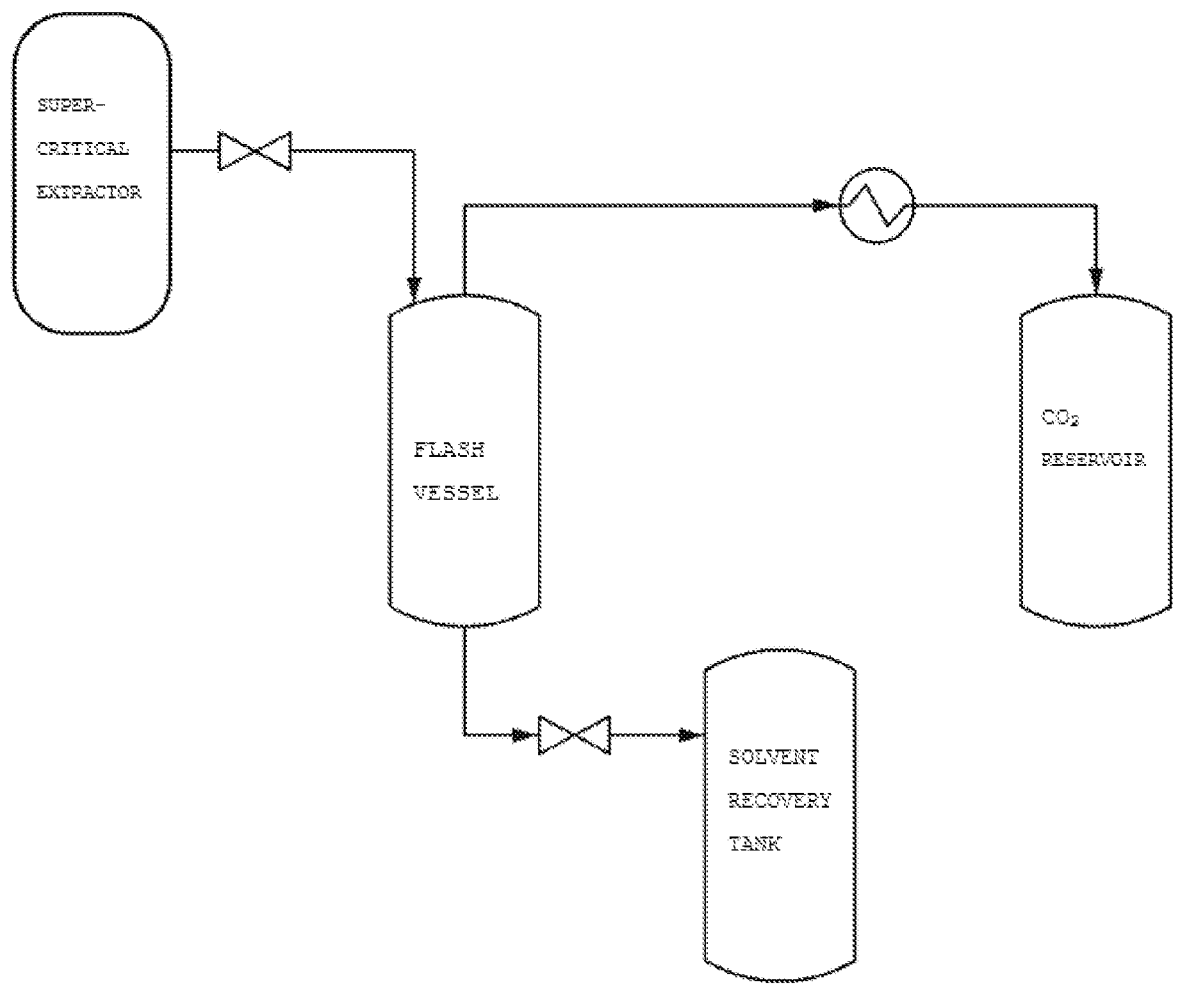
FIG. 2 is a schematic diagram schematically showing a solvent separation method and a solvent separation apparatus of Comparative Example.

Hereinafter, the present invention will be described in detail in order to facilitate understanding of the present invention. The terms and words used in the present specification and claims should not be construed to be limited to ordinary or dictionary terms and the inventor should properly define the concept of the term to describe its invention in the best way possible. The present invention should be construed in accordance with the meaning and concept consistent with the technical idea of the present invention.

The present invention provides a solvent separation method including:

1) introducing, into a first flash vessel, a fluid which includes carbon dioxide and a solvent and has passed through a supercritical extractor;

2) introducing, into a second flash vessel, the fluid which has passed through the first flash vessel; and 3) discharging and recovering the carbon dioxide and the solvent which have passed through the second flash vessel, respectively, wherein the pressure of the first flash vessel is 40-100 bar, and the pressure of the second flash vessel is 1-30 bar.

Hereinafter, the present invention will be described in more detail for each step.

The present invention is characterized by extracting a solvent through a supercritical extraction method using carbon dioxide, and is characterized by including step 1) of introducing, into a first flash vessel, a fluid which includes carbon dioxide and a solvent and has passed through a supercritical extractor.

The carbon dioxide ($CO_2$) is in a gaseous state at room temperature and atmospheric pressure but becomes a critical state which may not distinguish between gas and liquid when it exceeds a certain temperature and high pressure limit called a supercritical point. The carbon dioxide in this critical state is called a supercritical carbon dioxide.

The carbon dioxide has a critical temperature of 31.1° C. and a critical pressure of 73.8 bars. Therefore, the supercritical extractor is characterized by maintaining the temperature and pressure thereof above the critical temperature and critical pressure of the carbon dioxide. Specifically, the extractor is characterized by being maintained at a pressure of 73.8-300 bar and a temperature of 31.1-80° C.

On the other hand, the solvent used in the present invention is characterized by being one or more selected from the group consisting of water, ethanol, methanol, propanol, ethyl acetate, acetone and a nucleic acid. Specifically, the solvent means a solvent separated from a solvent mixture by the supercritical carbon dioxide in the supercritical extractor.

More specifically, the solvent means a solvent having a higher solubility with respect to the carbon dioxide in the solvent mixture included in the supercritical extractor. For example, when the solvent mixture is a mixture of water and ethanol, the solvent according to the present invention, which is dissolved in the supercritical carbon dioxide and discharged to the first flash vessel, becomes ethanol having a higher solubility.

When the temperature of the supercritical extractor is lower than 31.1° C., the supercritical carbon dioxide may not be easily formed; when the temperature exceeds 80° C., the temperature is unnecessarily increased regardless of the increase in extraction yield, so that the process cost may be increased.

Likewise, when the pressure of the supercritical extractor is lower than 73.8 bars, the supercritical carbon dioxide may not be easily formed; when the pressure exceeds 300 bars, the pressure is unnecessarily increased regardless of the increase in extraction yield, so that the process cost may be increased.

In addition, it is preferable that the supercritical extractor maintains the above temperature and pressure for 6-9 hours, preferably 5-8 hours. In the case of less than 6 hours, the solvent extraction effect may be insufficient, and in the case of exceeding 9 hours, the solvent extraction effect is not increased so much but the process time becomes longer, so that the process efficiency may be deteriorated.

Generally, after the supercritical extraction of the solvent, $CO_2$ is transferred to the flash vessel, separated into $CO_2$ in a gas phase and a solvent in a liquid phase, respectively and reused through depressurization. $CO_2$ recovered in the gas phase is again used in the extraction via heat exchange/depressurization, and the solvent present in the liquid phase in the flash vessel is recovered in atmospheric pressure and room temperature conditions by opening the lower valve of the flash vessel and is reused.

However, in this case, the liquid solvent present in the flash vessel in a high pressure condition is suddenly depressurized to atmospheric pressure, and thus some solvent is vaporized and lost. Also, as the pressure is rapidly reduced, the temperature is rapidly decreased, and thus the discharge of solvent and the freezing phenomenon of the recovery line occur, and in the worst case, a process problem of clogging the line also occurs.

Accordingly, the present invention is characterized in that the pressure of the extracted solvent is reduced stepwise to separate the solvent. Specifically, the present invention is characterized in that two or more of flash vessels are connected in series, and the temperature and pressure conditions of the carbon dioxide and solvent are changed stepwise, thereby minimizing the amount of the solvent lost by vaporization due to the rapid pressure variation to increase the recovery rate of the solvent and to finally increase the reuse rate of the solvent.

In the present invention, the term "first flash vessel" and "second flash vessel" are terms used to distinguish two or more of flash vessels. The first flash vessel may be a flash vessel directly connected to the supercritical extractor, and the second flash vessel may be a flash vessel connected to the first flash vessel. Also, there may be third and fourth flash vessels other than the second flash vessel.

The fluid which includes the carbon dioxide and the solvent and has passed the supercritical extractor of the present invention may be introduced into the first flash vessel for separating the fluid into the carbon dioxide and the solvent, and the present invention is characterized in that the pressure of the first flash vessel is maintained at 40-90 bar, specifically 50-90 bar, and the temperature thereof is maintained at 10-30° C., preferably 15-25° C.

When the pressure of the first flash vessel is lower than 40 bar or the temperature thereof exceeds 30° C., the solvent may be vaporized to decrease the recovery rate; when the pressure exceeds 100 bar or the temperature is lower than 10° C., $CO_2$ to be recovered to the upper portion of the first flash vessel may be excessively dissolved in the lower solvent of the flash vessel.

The step 2) of the present invention is characterized in that the fluid having passed the first flash vessel is not discharged and recovered directly in atmospheric pressure and room temperature conditions but is introduced into the second flash vessel. As described above, in the solvent separation method of the present invention, two or more of flash vessels are connected in series to perform the separation of the carbon dioxide and the solvent stepwise.

The second flash vessel of present invention is characterized in that the pressure is maintained at 10-30 bar, preferably 10-20 bar, and the temperature is maintained at 10-30° C., preferably 15-25° C.

As in the first flash vessel, when the pressure of the second flash vessel is lower than 1 bar or the temperature thereof exceeds 30° C., the solvent may be vaporized to decrease recovery rate; when the pressure exceeds 30 bar or temperature is lower than 10° C., $CO_2$ to be recovered to the upper portion may be excessively dissolved in the lower solvent of the flash vessel. In addition, in this case, when the solvent is recovered in the atmospheric pressure condition, $CO_2$ dissolved in the solvent may be vaporized to cause a loss of the solvent.

The step 3) of the present invention is characterized in that the carbon dioxide and the solvent which have passed through the supercritical extractor, the first flash vessel and the second flash vessel are finally recovered.

Specifically, the solvent discharged from the second flash vessel through a pressure reducing valve present in the lower portion of the second flash vessel is recovered in atmospheric pressure and room temperature conditions.

Since the carbon dioxide is present as a gas under the second flash vessel operating condition, the carbon dioxide is pressurized and cooled through the compressor and the heat exchanger connected to the upper portion of the second flash vessel and is recovered in a liquid state in the carbon dioxide reservoir. Also, the solvent is recovered in a liquid state in the solvent recovery tank connected to the lower portion of the second flash vessel.

The recovered carbon dioxide and solvent may be reused by recirculation in the supercritical extractor, respectively.

Meanwhile, the present invention is characterized in that the supercritical extracted solvent is depressurized stepwise to minimize the lost amount of the solvent, thereby increasing the recovery rate of the solvent, wherein the solvent recovery rate is 95% or more, specifically 96% or more, more specifically, 96.5% or more, still more specifically 97% or more.

The solvent recovery rate (%) may be calculated by an equation of (the total amount of the solvent recovered in a liquid state in the recovery tank/the total amount of the supercritical extracted solvent)×100%.

In addition, the present invention provides a solvent separation apparatus on the basis of the solvent separation method.

Specifically, the solvent separation apparatus of the present invention includes:

a) a first flash vessel into which a fluid, which includes carbon dioxide and a solvent and has passed a supercritical extractor, is introduced;

b) a second flash vessel into which a fluid having passed the first flash vessel is introduced; and c) a solvent recovery tank connected to a lower portion of the second flash vessel and configured to store the discharged and recovered solvent, wherein the pressure of the first flash vessel is 40-100 bar, and the pressure of the second flash vessel is 1-30 bar.

In addition, the solvent separation apparatus may further include a carbon dioxide reservoir connected to the upper portion of the second flash vessel and configured to store the discharged and recovered carbon dioxide.

Hereinafter, embodiments of the present invention will be described in detail so that those skilled in the art can easily carry out the present invention. The present invention may, however, be embodied in many different forms and should not be construed as limited to the embodiments set forth herein.

Example 1

In order to extract and separate ethanol from a mixture of water and ethanol through supercritical carbon dioxide, a supercritical fluid which includes carbon dioxide and ethanol and has passed through the supercritical extractor operated at specifically 150 bar and 70° C. was introduced into a first flash vessel operated at 50 bar and 20° C., and then was introduced into a second flash vessel operated at 10 bar and 20° C. Also, the carbon dioxide was pressurized and cooled through a compressor and a heat exchanger connected to the upper portion of the second flash vessel and was recovered in a liquid state through a carbon dioxide reservoir, and the ethanol was recovered in a liquid state in atmospheric pressure and room temperature conditions through a pressure reducing valve present in the lower portion of the second flash vessel.

Example 2

Ethanol was recovered in the same manner as Example 1 except that the first flash vessel was operated at 50 bars and 30° C. and the second flash vessel was operated at 30 bars and 30° C.

Example 3

Ethanol was recovered in the same manner as Example 1 except that the first flash vessel was operated at 70 bars and 15° C. and the second flash vessel was operated at 30 bars and 20° C.

Comparative Example 1

Ethanol was recovered in the same manner as Example 1 except that only the first flash vessel operated at 50 bars and 20° C. was used to directly discharge and recover ethanol in atmospheric pressure and room temperature conditions at 50 bars and 20° C.

Comparative Example 2

Ethanol was recovered in the same manner as Example 1 except that the first flash vessel was operated at 120 bars and 20° C.

Comparative Example 3

Ethanol was recovered in the same manner as Example 1 except that the first flash vessel was operated at 120 bars and 20° C., and the second flash vessel was operated at 50 bars and 20° C.

Experimental Example: Measurement of Ethanol Recovery Rate

In order to calculate the recovery rate of the ethanol recovered in Examples and Comparative Examples, the flow rate of carbon dioxide, water and ethanol which were extracted from the supercritical extractor and introduced into the first flash vessel, and the flow rate of carbon dioxide, water, and liquid ethanol which were recovered to the recovery tank were measured, and the measuring results and the solvent recovery rate are shown in Table 1.

TABLE 1

|  |  | First flash vessel | Recovery tank | Solvent recovery rate |
|---|---|---|---|---|
| Example 1 | $CO_2$ (kg/hr) | 40.9 | 0.031 | 97.2% |
|  | $H_2O$ (kg/hr) | 0.4 | 0.389 |  |

TABLE 1-continued

|  |  | First flash vessel | Recovery tank | Solvent recovery rate |
|---|---|---|---|---|
|  | EtOH (kg/hr) | 2.88 | 2.8 |  |
| Example 2 | $CO_2$ (kg/hr) | 40.9 | 0.037 | 96.1% |
|  | $H_2O$ (kg/hr) | 0.4 | 0.385 |  |
|  | EtOH (kg/hr) | 2.88 | 2.77 |  |
| Example 3 | $CO_2$ (kg/hr) | 40.9 | 0.06 | 96.5% |
|  | $H_2O$ (kg/hr) | 0.4 | 0.388 |  |
|  | EtOH (kg/hr) | 2.88 | 2.77 |  |
| Comparative Example 1 | $CO_2$ (kg/hr) | 40.9 | 0.021 | 90.2% |
|  | $H_2O$ (kg/hr) | 0.4 | 0.359 |  |
|  | EtOH (kg/hr) | 2.88 | 2.6 |  |
| Comparative Example 2 | $CO_2$ (kg/hr) | 40.9 | 0.02 | 92.0% |
|  | $H_2O$ (kg/hr) | 0.4 | 0.37 |  |
|  | EtOH (kg/hr) | 2.88 | 2.65 |  |
| Comparative Example 3 | $CO_2$ (kg/hr) | 40.9 | 0.02 | 89.9% |
|  | $H_2O$ (kg/hr) | 0.4 | 0.36 |  |
|  | EtOH (kg/hr) | 2.88 | 2.59 |  |

* Solvent recovery rate = (the total amount of solvent recovered in liquid state in the recovery tank/the total amount of supercritical extracted solvent) × 100%

As shown in Table 1, it can be seen from Examples of the present invention that the first and second flash vessels were arranged in series and the pressure of ethanol was reduced stepwise to improve the solvent recovery rate. Also, it can be seen from Comparative Example 1 that the pressure was rapidly reduced from high pressure to atmospheric pressure once in one step, so that the solvent recovery rate was inferior to those in Examples.

In addition, it can be seen from Comparative Example 2 that the pressure range of the first flash vessel was beyond the pressure range of the first flash vessel of the present invention, so that the solvent recovery rate was inferior to those in Examples due to the rapid pressure difference between the first flash vessel and the second flash vessel. Also, it can be seen from Comparative Example 3 that the pressure ranges of the first flash vessel and the second flash vessel were beyond the pressure ranges of the first flash vessel and the second flash vessel of the present invention, so that the solvent recovery rate was inferior to those in Examples due to the rapid pressure difference between the first flash vessel and the second flash vessel and between the second flash vessel and the recovery tank.

The foregoing description of the present invention has been presented for purposes of illustration only, and it will be understood by those skilled in the art to which the present invention belongs that various changes in form and details may be made therein without departing from the technical concept or essential features of the invention. It is therefore to be understood that the above-described embodiments are illustrative in all aspects and not restrictive.

The invention claimed is:

1. A solvent separation method comprising:
   1) introducing a supercritical fluid having passed through a supercritical extractor into a first flash vessel, wherein the supercritical fluid comprises carbon dioxide and a solvent;
   2) introducing supercritical fluid which has passed through the first flash vessel into a second flash vessel; and
   3) discharging and recovering carbon dioxide and solvent which have passed through the second flash vessel, respectively,
   wherein a pressure of the first flash vessel is 50-90 bar, and a pressure of the second flash vessel is 10-30 bar,
   wherein discharging and recovering the solvent is carried out at atmospheric pressure and room temperature.

2. The method of claim 1, wherein temperatures of the first flash vessel and the second flash vessel are individually maintained at 10-30° C.

3. The method of claim 1, wherein the supercritical extractor is maintained at a pressure of 73.8-300 bar and a temperature of 31.1-80° C.

4. The method of claim 1, wherein the carbon dioxide is pressurized and liquefied through a compressor and a heat exchanger connected to an upper portion of the second flash vessel and recovered in a liquid state in a carbon dioxide reservoir, and the solvent is recovered in a liquid state in a solvent recovery tank connected to a lower portion of the second flash vessel.

5. The method of claim 1, wherein the recovered carbon dioxide is circulated to the supercritical extractor to be reused.

6. The method of claim 1, wherein the solvent is one or more selected from the group consisting of water, ethanol, methanol, propanol, ethyl acetate, acetone, and a nucleic acid.

7. The method of claim 1, wherein a recovery rate of the solvent is 95% or more.

\* \* \* \* \*